United States Patent [19]

Patzer

[11] Patent Number: 5,578,059
[45] Date of Patent: Nov. 26, 1996

[54] ANTI-REFLUX VALVE WITH ENVIRONMENTAL BARRIER

[75] Inventor: Charles R. Patzer, Ashville, Ohio

[73] Assignee: Medex, Inc., Hilliard, Ohio

[21] Appl. No.: 513,575

[22] Filed: Aug. 10, 1995

Related U.S. Application Data

[63] Continuation of Ser. No. 216,640, Mar. 23, 1994, abandoned, which is a continuation-in-part of Ser. No. 160,047, Nov. 30, 1993, abandoned.

[51] Int. Cl.$^6$ .................................................. A61M 5/00
[52] U.S. Cl. ........................ 604/249; 604/256; 251/149.1
[58] Field of Search .............................. 604/30, 33, 167, 604/246, 247, 249, 256; 251/149.1, 149.2, 149.6; 137/846, 849, 854

[56] References Cited

U.S. PATENT DOCUMENTS

| | | |
|---|---|---|
| 3,977,400 | 8/1976 | Moorehead . |
| 3,986,508 | 10/1976 | Barrington . |
| 3,994,293 | 11/1976 | Ferro . |
| 4,326,569 | 4/1982 | Vaillancourt . |
| 4,511,359 | 4/1985 | Vaillancourt . |
| 4,535,820 | 8/1985 | Raines . |
| 4,601,703 | 7/1986 | Herlitze . |
| 4,610,665 | 9/1986 | Matsumoto et al. . |
| 4,683,916 | 8/1987 | Raines . |
| 4,765,588 | 8/1988 | Atkinson . |
| 4,768,568 | 9/1988 | Fournier et al. . |
| 4,857,062 | 8/1989 | Russell . |
| 4,874,377 | 10/1989 | Newgard et al. . |
| 4,886,507 | 12/1989 | Patton et al. . |
| 4,895,346 | 1/1990 | Steigerwald . |
| 4,909,798 | 3/1990 | Fleischhacker et al. . |
| 4,917,668 | 4/1990 | Haindl . |
| 4,950,257 | 8/1990 | Hibbs et al. . |
| 4,966,588 | 10/1990 | Rayman et al. . |
| 5,000,745 | 3/1991 | Guest et al. . |
| 5,041,095 | 8/1991 | Littrell . |
| 5,049,128 | 9/1991 | Duquette . |
| 5,059,186 | 10/1991 | Yamamoto et al. . |
| 5,092,857 | 3/1992 | Fleischhacker . |
| 5,104,389 | 4/1992 | Deem et al. . |
| 5,135,489 | 9/1982 | Jepson et al. . |
| 5,163,922 | 11/1992 | McElveen, Jr. et al. ............... 604/249 |
| 5,190,067 | 3/1993 | Paradis et al. . |
| 5,195,980 | 3/1993 | Catlin . |
| 5,203,775 | 4/1993 | Frank et al. . |
| 5,207,656 | 5/1993 | Kranys . |
| 5,211,634 | 5/1993 | Vaillancourt . |
| 5,215,537 | 6/1993 | Lynn et al. . |
| 5,242,393 | 9/1993 | Brimhall et al. ......................... 604/86 |
| 5,242,423 | 9/1993 | Goodsir et al. . |
| 5,251,873 | 10/1993 | Atkinson et al. . |
| 5,269,763 | 12/1993 | Boehmer et al. ...................... 604/167 |
| 5,269,771 | 12/1993 | Thomas et al. . |
| 5,312,362 | 5/1994 | Pfolsgraf et al. ....................... 604/167 |
| 5,441,487 | 8/1995 | Vedder ..................................... 604/167 |
| 5,470,319 | 11/1995 | Mayer ..................................... 604/167 |

FOREIGN PATENT DOCUMENTS

| | | |
|---|---|---|
| 3042229 | 5/1982 | Germany . |
| 3242870 | 6/1983 | Germany . |
| 0111723 | 6/1984 | Germany . |
| 3303718 | 10/1984 | Germany . |
| 2012919 | 8/1979 | United Kingdom ................... 604/247 |

*Primary Examiner*—Corrine M. McDermott
*Attorney, Agent, or Firm*—Wood, Herron & Evans, P.L.L.

[57] ABSTRACT

A medical site (10) includes a slit septum environmental barrier (12) held across the inlet opening (76) of housing (16). Site (10) includes a disc anti-reflux valve (14) below the inlet (76) of housing (16).

3 Claims, 2 Drawing Sheets

5,578,059

ANTI-REFLUX VALVE WITH ENVIRONMENTAL BARRIER

RELATED APPLICATION

This application is a continuation of application Ser. No. 08/216,640 filed Mar. 23, 1994 now abandoned, which is a continuation-in-part of application Ser. No. 08/160,047, filed Nov. 30, 1993 now abandoned, and assigned to the assignee hereof.

BACKGROUND OF THE INVENTION

I. Field of the Invention

The present invention relates to medical sites through which fluid may be injected into or withdrawn from a patient without requiring use of sharp needles.

II. Description of Prior Art

In many medical situations, it is typical to provide a fluidfilled (e.g., saline) line coupled to a patient's circulatory system via a catheter inserted into the patient such as through the arm. A site is coupled in series with the fluid-filled line to provide access to the patient's circulatory system without further puncturing the patient such as with additional needles or catheters or the like. The site has a valve, such as a rubber septum or the like, through which access to the fluid line is by piercing through the septum with a needle, for example. When access is made, medications may be injected into the patient through the site and fluid line. Similarly, blood samples may be taken from the patient by withdrawal through the site. Examples of such uses are shown in U.S. Pat. Nos. 4,874,377; 5,148,811; 5,203,775; 5,221,271; and co-pending application Ser. No. 08/003,790, filed Jan. 13, 1993, the disclosures of all of which are hereby fully incorporated herein by reference.

As shown in those patents, it is possible to inject medicines into, or withdraw blood from, the patient through the site rather than by a further needle stick of the patient. But, as discussed in aforementioned U.S. Pat. No. 5,203,775, the use of sharp needles, even with sites, presents hazards to the medical personnel using the sites due the risk of needle sticks which could transmit disease.

The risk of needle sticks is greatly reduced when blunt cannulas, such as the distal plastic end of a typical syringe, can be used to access the fluid line through the valve of the site rather than a sharp needle. And while various proposals have been made to permit use of blunt cannulas, none have apparently met with much success for one reason or another.

One proposal for eliminating needles involves use of a slit septum as the site valve. The slit septum opens under pressure of a blunt cannula thereagainst to allow the blunt cannula to pass into and through the slit of the septum and into communication with the fluid line. While a slit septum has certain advantages in the drive to eliminate needles, it is not without a serious drawback. In particular, a slit across the septum tends to weaken the valve such that it may not be rigid enough to withstand back pressure from the fluid line when the cannula is removed. In such an event, the integrity of the valve is jeopardized which could result in fluid leakage from the valve with the attendant undesirable risks of infection and/or disease transmission.

SUMMARY OF THE INVENTION

The present invention permits utilization of a slit septum member for a blunt cannula-accessible device but which does not suffer the drawback of a weakened valve that cannot withstand back pressure when closed. To this end, and in accordance with the present invention, a medical device having a housing with an inlet and outlet and a blunt-cannula openable one-way or back check valve situated therebetween is provided with a slit septum environmental barrier across the housing inlet. The check valve withstands back pressure from the fluid line when the slit septum is not opened so as to prevent fluid from backing up against the back side of the slit septum, yet allows fluid to flow from the slit septum to the fluid path under pressure such as from a syringe or other source of fluid directed through the slit septum and against the check valve. Yet further, the check valve is situated relative the slit septum such that insertion of a blunt cannula into and through the slit septum will also cause the check valve to open such as by a portion of the blunt cannula impacting against the check valve to deform and forcibly hold same open and permit two-way fluid communication therethrough.

By virtue of the foregoing, there is thus provided a medical site which has the advantage of a slit septum as an environmental barrier and with which blunt cannulas may be utilized, but which does not suffer the drawback of leakage which might normally be expected to occur where the valve function is provided by a slit septum. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF THE DRAWINGS

Figure 1:
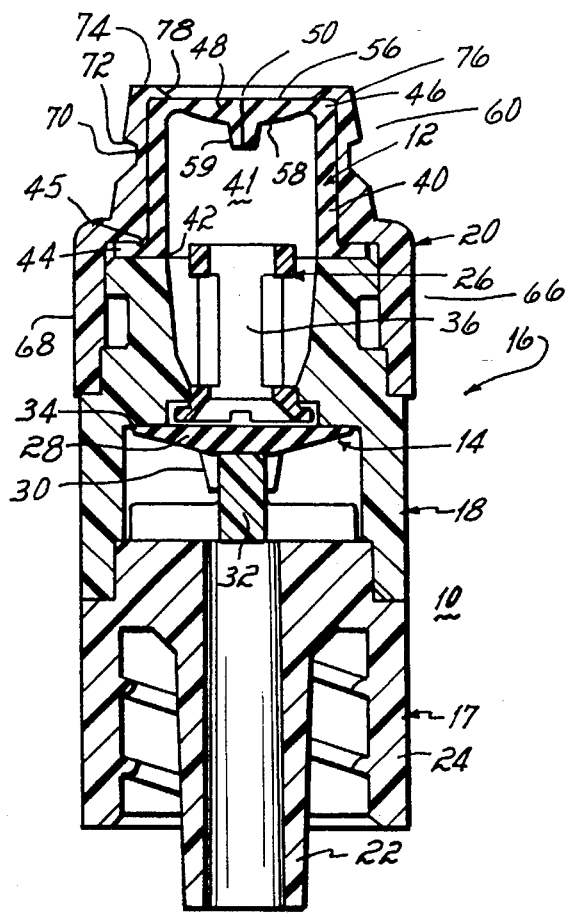
FIG. 1 is a cross-sectional view of a medical site having a disc anti-reflux check valve incorporating a slit septum environmental barrier in accordance with the principles of the present invention.

With reference to FIG. 1, there is shown in cross-section an embodiment of a medical site 10 incorporating the features of the present invention. Site 10 in the embodiment shown here includes a slit septum elastomeric (e.g., silicon or polyisoprene rubber) barrier 12 and an anti-reflux disc valve 14 held within plastic (e.g. polycarbonate, Dow Isoplast, rigid PVC, or Ektar) housing 16. Plastic housing 16 includes three portions, namely, male luer lock fluid connector 17, actuator housing 18 and tapered thread housing 20, all bonded together such as with solvent, UV cured adhesive or ultrasonic welding, or they may be frictionally or snap fit together. Connector 17 is a fluid port and includes a standard ISO or ANSI luer taper 22 and locking collar 24 for fluid connection to a fluid line (not shown) coupled, for example, to a patient. Actuator housing 18 contains disk valve 14 comprised of actuator 26 and resilient disc 28, the underside skirt 30 of which is seated on nipple 32 of housing 17 projecting into housing 18. Disc 28 normally bears against valve seat 34 of housing 18 to stay closed. Disc 28 will open if fluid pressure from above is greater than the pressure from below, but not vice versa and, thus, functions as a one-way or check valve. Disc 28 also opens under pressure such as from actuator 26 pushed thereagainst by which to permit two-way fluid communication. Actuator 26 is open through its interior 36 to permit fluid to flow therethrough and over disc 28 when disc valve 14 is opened. Fluid may thus pass in from barrier 12 (when it is opened) and out of the lower or outlet end of housing 18 such as via connector 17 (fluid may also flow in the reverse direction).

Focusing now on barrier 12 and its associate housing 20, barrier 12 has a tubular or cylindrical body 40 defining a fluid path 41 therein. Body 40 has an inner diameter of about 0.195 inch and an outer diameter of about 0.246 inch. Extending outwardly about 0.042 inch from the bottom edge 42 of body 40 is an annular lip or flange 44. Actuator housing 18 acts as a support member on which flange 44 sets. Thread housing 20 and actuator housing 18 cooperate to grip barrier 12 with flange 44 therebetween. An annular ring 45 is interposed between housing 20 and flange 44. Annular ring 45 may be formed as part of housing 20 and depend therefrom to dig into flange 44 adjacent edge 42 to deform same as seen in FIG. 1. Ring 45 securely holds barrier 12 to housing 16 and prevents barrier 12 from being extruded inwardly. Ring 45 could, alternatively, be formed on housing 18.

The top edge 46 of body 40 is integrally joined to a closing web 48 to provide an environmental barrier to fluid path 41. To facilitate use of barrier 12, a 0.150 inch slit 50 is formed through web 48 to receive a blunt cannula such as male taper 52 of a male luer lock 54, for example (see FIG. 4), into barrier 12 through slit 50. Web 48 has a generally flat top 56 and a convex underside 58 and may include structure such as one or more ribs or steps (not shown) to assist in keeping slit 50 in a closed and sealed state until taper 52 bears thereagainst. Extending from underside 58 and along slit 50 may be duckbill lips 59.

Housing 20 is a single injection molded piece and has an upper portion 60 (see FIG. 2) designed to hold tubular body 40 of barrier 12 and to mate with the interior threads 62 of locking nut 64 of male luer lock 54. Housing 20 also includes a lower portion 66 designed to matingly fit over actuator housing 18 to be secured thereto. Lower portion 66 may also be knurled (not shown) about its exterior surface 68 to facilitate handling of site 10 by a user (not shown). Upper portion 60 of housing 20 is sized thin enough to fit into nut 64, yet robust enough to secure to luer lock 54 while protecting barrier 12 in normal use. To this end, the upper portion 60 of housing 20 may be considered as having two aspects, one being a thin-walled housing cylinder 70 and the other being a wedging member such as a pair of tapered threads 72. Thin-wall cylinder 70 is defined as the cylindrical aspect of housing 20 adjacent and coaxial with tubular body portion 40 of barrier 12 and is about 0.012 inch thick. Cylinder 70 has an inner diameter of about 0.246 inch to match to the outer diameter of body 40, and an outer diameter of about 0.270 inch. With the thin-wall, it will be appreciated that cylinder 70 is sized to be received into the interior of locking nut 64 of luer lock 54, which has a minimum inner diameter of about 7 mm (0.27 inch). However, cylinder 70 is not itself thick enough to guard barrier 12 or withstand even normal use, nor does cylinder 70 itself lock to luer lock 54. The provision of a tapered wedge member such as one or more threads 72 solves these problems.

Figure 2:
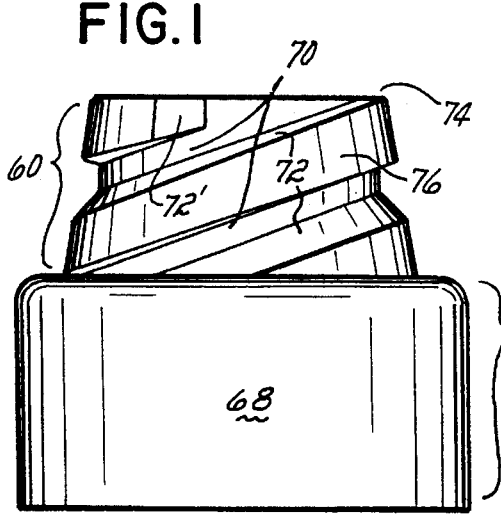
FIG. 2 is a side view of the tapered thread housing of FIG. 1.
Figure 3:
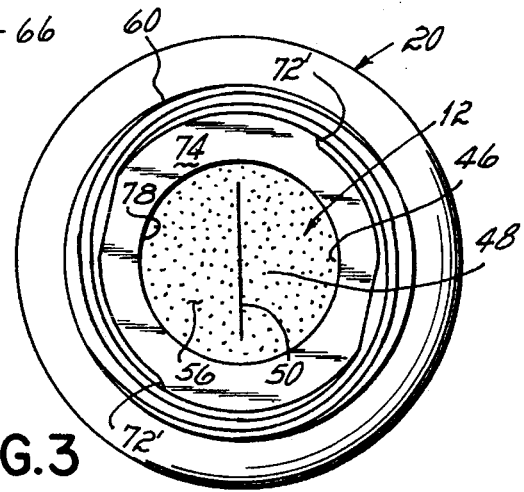
FIG. 3 is a top view of the site of FIG. 1.

With further reference to FIGS. 2 and 3, it may be seen that tapered threads 72 are formed about and spiral downwardly from top end 74 of cylinder 70. The start points 72' of the threads 72 are on opposite sides of cylinder 70 so that threads 72 intertwine as seen in FIG. 3. Cylinder 70 defines the minor diameter of threads 72 and the distal or outer edge 76 of each thread 72 defines the major diameter thereof. The major diameter 76 extends radially outwardly of cylinder 70 only slightly (about 0.008 inch) at top end 74 and is thus narrow at the top end 74 of cylinder 70, to be sized to still be received within the interior of locking nut 64. As threads 72 progress spirally downwardly towards lower portion 66, the major diameter 76 increases in thickness to about 0.036 inch such that the outer diameter thereof is larger than the inner diameter of lock nut 64. Thus, at the lower end of threads 72 spaced from top end 74, the threads are wider than at top end 74. Threads 72 are 10 pitch with double start and cylinder 70 is about 0.171 inch long or tall to be coextensive with tubular body 40 of barrier 12 such that the top 56 of slit web 48 is at or generally flush with opening 70 at top end 74 of housing 20 (and cylinder 70) to be aseptically cleaned by wiping thereacross. Top end 74 of housing 12 defines a lip projecting inwardly from cylinder 70 about 0.023 inch to overlie top edge 46 of barrier 12 and help hold barrier 12 in place with the top surface 56 thereof generally flush with housing top end 74. Top surface 56 is thus accessible via inlet opening 78 of cylinder 70 to be cleaned with a gauze pad (not shown), for example, wiped thereacross.

It will be appreciated that the tapered threads 72 are integral with cylinder 70 and function to strengthen cylinder 70 without making housing 20 too large to mate with lock nut 64, yet provide a positive and gradual locking function between site 10 and luer lock 54.

Figure 4:
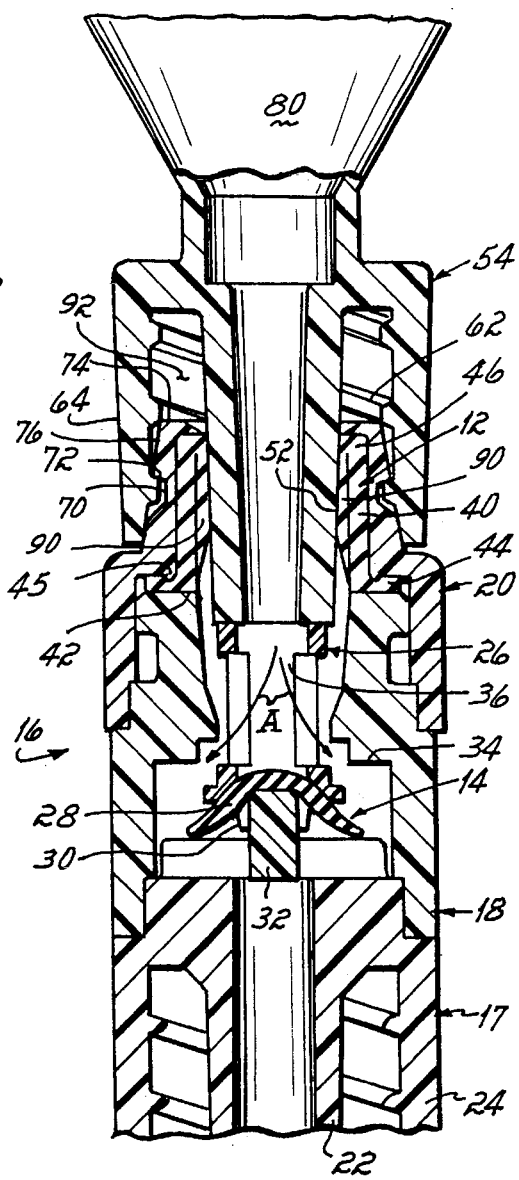
FIG. 4 is a cross-sectional view of the site of FIG. 1 with a standard ISO or ANSI male luer lock attached thereto for purposes of explaining the principles of the present invention.

In use, flat top 56 of web 48 is wiped clean and, as seen in FIG. 4, taper 52 of luer lock 54 (luer lock 54 could be part of a syringe 80 as is well known) is inserted into and through slit 50 of web 48. As that occurs, the top end 74 of upper portion 60 of housing 20 is received into the interior of locking nut 64. Nut 64 is rotated as it passes over top end 74. Threads 62 of luer lock 54 and tapered thread 72 of housing 20 cooperate to draw taper 52 into actuator housing 18. Taper 52 then passes into fluid path 41 and impacts against actuator 26 moving it downwardly into disc 28 to thereby open same for fluid to flow through taper 52 and actuator 26, over disc 28 and through outlet luer taper 22 of connector 17 along the path of Arrows A (or vice versa) to complete a fluid connection through site 10. Also, the portions of web 48 to either side of slit 50 flex downwardly and outwardly to either side of taper 52 like lips, as at 90 in FIG. 4. At the same time, lock nut 64 does not merely threadably engage to housing 20 as would be typically expected, but instead is wedged thereagainst by coaction of the material of plastic housing upper portion 60, and particularly tapered threads 72, and the major diameter 92 of locking collar 64 to thereby securely hold male luer lock 54 to site 10. Luer lock 54 may be easily removed by reverse rotation of locking collar 64 to thereby release the wedge and remove taper 54 which also recloses disc valve 14 and slit septum barrier 12 which thereafter isolates disc valve 14 and fluid path 41 from the environment.

Figure 5:
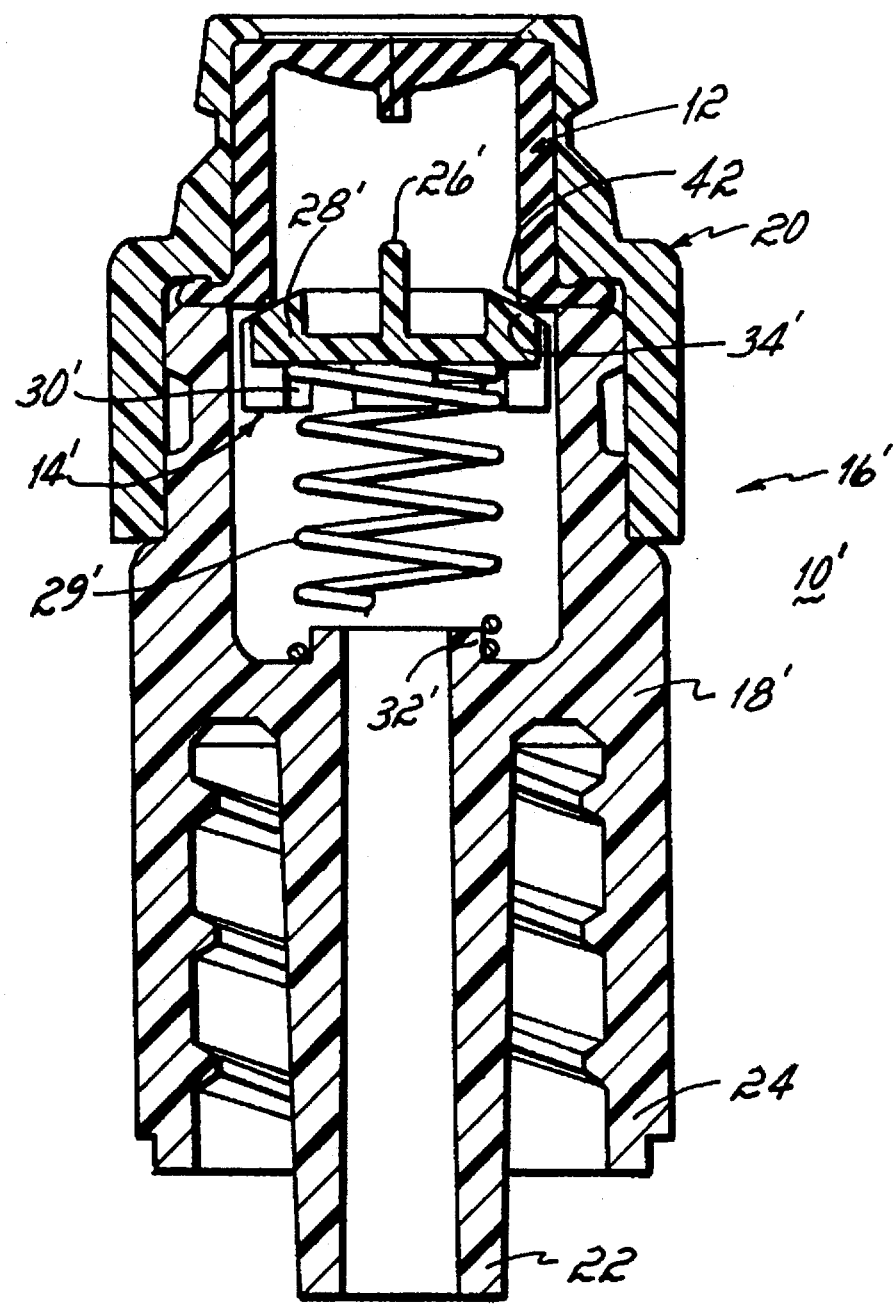
FIG. 5 is a cross-sectional view of an alternative version of a disc anti-reflux valve to which an environmental barrier is applied in accordance with the principles of the present invention.

With reference to FIG. 5, an alternative version of a disc valve 14' is shown which may advantageously be provided with the environmental barrier 12 as in the case of site 10 of FIG. 1. To this end, site 10' of FIG. 5 includes barrier 12 and thread housing 20 as above-described. However, connector 17 and actuator housing 18 are combined into one housing piece 18' to support spring-biased disc reflux valve 14'. Disc valve 14' includes a plastic disc 28' which is biased closed by spring 29' against valve seat 34' defined at the lower edge 42 of barrier 12. Spring 29' seats over mouth 32' of housing 18' and within a groove 30' defined under disc 28'. Extending up from disc 28' is actuator piece 26' to cooperate with taper 52 passed through barrier 12 to push disc 28' away from valve seat 34' to permit fluid communication through housing 16' similar to that in the case of site 10 of FIG. 1. Also, as is clearly seen in FIGS. 1 and 5, barrier 12 is separate and not integrally connected to the disc valve 14 or 14'.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the secondary or check valve of the site of aforementioned parent application Ser. No. 08/160,047 could be disc valve 14 as described herein. Additionally, the fluid port of connector 17 could instead be provided by a Y-site or T-shaped sample or injection site, or a tubing port, as will be readily appreciated. Additionally, instead of the major diameter 76 of the wedging member tapering outwardly, that outer surface could be held at a fixed diameter with the minor diameter of threads 72 tapering outwardly instead. Or both the minor and major diameters of thread(s) 72 could taper outwardly. Further, the thread tapering could be in discrete portions of the overall thread length or the threads may be truncated and traverse only partway down cylinder 70. Moreover, although the wedging member is described as a thread structure or pair of threads, a single thread or other tapered wedging member structure may be employed to functionally thicken or strengthen cylinder 70 and also lock within luer lock 54. Additionally, both the major and minor diameters may be uniform, i.e., non-tapered such as by chasing a thread down a cylinder. The invention in its broader aspects is therefore not limited to the specific details, representative apparatus and method and illustrative examples shown and described. Accordingly, departures may be made from such details without departing from the scope or spirit of applicant's general inventive concept.

Having described the invention, what is claimed is:

1. A medical valve including a housing having an inlet and an outlet and a normally closed disc valve, valve actuator, and valve seat situated therebetween, the disc valve being openable by a blunt cannula inserted through the inlet and acting upon the valve actuator, the disc valve being mounted for movement by the valve actuator away from the valve seat within the housing to create an uninterrupted annular through opening between the valve seat and the disc valve, and an environmental barrier separate from the disc valve and extending completely across the housing inlet, the environmental barrier including an elastomeric slit septum, the slit being normally biased closed and being openable under pressure of the blunt cannula to allow the blunt cannula to pass through the slit to the disc valve.

2. In the medical device of claim 1, the improvement further comprising providing duckbill lips between the environmental barrier and the disc valve, the duckbill lips extending along the slit.

3. In the medical device of claim 2 wherein the duckbill lips are formed integral with the environmental barrier.

* * * * *